(12) United States Patent
Beck et al.

(10) Patent No.: US 8,876,787 B2
(45) Date of Patent: Nov. 4, 2014

(54) ANTI-FREE-FLOW MECHANISM FOR ENTERAL FEEDING PUMPS

(75) Inventors: Kent Beck, Layton, UT (US); Jason Bultman, Salt Lake City, UT (US); Jeff Juretich, Herriman, UT (US); Philip Eggers, Salt Lake City, UT (US); Ryan Federspiel, Salt Lake City, UT (US); Blake Allen, Murray, UT (US)

(73) Assignee: Zevex, Inc., Salt Lake City, UT (US)

( * ) Notice: Subject to any disclaimer, the term of this patent is extended or adjusted under 35 U.S.C. 154(b) by 371 days.

(21) Appl. No.: 12/416,041

(22) Filed: Mar. 31, 2009

(65) Prior Publication Data

US 2010/0082001 A1    Apr. 1, 2010

Related U.S. Application Data

(60) Provisional application No. 61/041,561, filed on Apr. 1, 2008.

(51) Int. Cl.
  *A61M 5/00* (2006.01)
  *A61M 39/24* (2006.01)
  *A61M 5/142* (2006.01)
  *A61M 39/28* (2006.01)

(52) U.S. Cl.
  CPC .............. *A61M 5/142* (2013.01); *A61M 39/24* (2013.01); *A61M 39/28* (2013.01); *A61M 2202/0482* (2013.01)
  USPC ........................................................ 604/250

(58) Field of Classification Search
  CPC . A61M 39/28; A61M 39/281; A61M 39/283; A61M 39/284; A61M 39/285; A61M 39/286; A61M 39/287

USPC .......................................... 604/250; 251/7, 9
See application file for complete search history.

(56) References Cited

U.S. PATENT DOCUMENTS

| | | | |
|---|---|---|---|
| 584,091 | A | 6/1897 | Leidich |
| 1,238,521 | A | 8/1917 | Janish, Jr. |
| 2,471,623 | A | 5/1949 | Hubbell |
| 2,518,165 | A | 8/1950 | Millard |
| 2,858,095 | A | 10/1958 | Harris et al. |
| 2,999,499 | A | 11/1961 | Willet |
| 3,213,882 | A | 10/1965 | Beatty |
| 3,329,391 | A | 7/1967 | Deane |

(Continued)

FOREIGN PATENT DOCUMENTS

| | | |
|---|---|---|
| EP | 0 150 666 | 9/1984 |
| EP | 0 276 356 | 8/1988 |

(Continued)

OTHER PUBLICATIONS

International Search Report for PCT/US2009/039034, Jun. 29, 2009.

*Primary Examiner* — Emily Schmidt
(74) *Attorney, Agent, or Firm* — Hodgson Russ LLP

(57) ABSTRACT

An anti-free-flow mechanism includes an occluder mechanism which is disposed along a segment of tubing and a mounting structure. The occluder mechanism is normally in a biased closed position, but may be moved into an open position by placement in the mounting structure. However, unless force is applied to keep the occluder mechanism in the mounting structure, the occluder will move relative to the mounting structure and return to the first, closed position.

14 Claims, 13 Drawing Sheets

(56) References Cited

U.S. PATENT DOCUMENTS

| | | |
|---|---|---|
| D208,753 S | 9/1967 | Curry |
| 3,497,175 A | 2/1970 | Koland |
| 3,707,972 A | 1/1973 | Villari et al. |
| 3,985,140 A | 10/1976 | Harris |
| 3,998,364 A | 12/1976 | Hollander |
| 4,037,596 A | 7/1977 | LeFevre et al. |
| 4,063,555 A | 12/1977 | Ulinder |
| 4,065,093 A | 12/1977 | Phillips |
| 4,106,675 A | 8/1978 | Taylor |
| 4,142,645 A | 3/1979 | Walton |
| 4,160,383 A | 7/1979 | Rauschenberger |
| 4,230,151 A | 10/1980 | Jonsson |
| 4,236,880 A | 12/1980 | Archibald |
| 4,373,524 A | 2/1983 | Leibinsohn |
| 4,381,591 A | 5/1983 | Barger et al. |
| 4,382,453 A | 5/1983 | Bujan et al. |
| 4,425,116 A | 1/1984 | Bilstad et al. |
| 4,430,073 A | 2/1984 | Bemis et al. |
| 4,453,295 A | 6/1984 | Laszczower |
| 4,498,843 A | 2/1985 | Schneider et al. |
| 4,524,802 A | 6/1985 | Lawrence et al. |
| 4,527,588 A | 7/1985 | Tseo et al. |
| 4,559,036 A | 12/1985 | Wunsch |
| 4,559,045 A | 12/1985 | Danby et al. |
| 4,579,553 A | 4/1986 | Urquhart et al. |
| 4,596,557 A | 6/1986 | Pexa |
| 4,624,663 A | 11/1986 | Danby et al. |
| 4,634,092 A | 1/1987 | Daniell et al. |
| 4,645,489 A | 2/1987 | Krumme et al. |
| 4,689,043 A | 8/1987 | Bisha |
| 4,728,324 A | 3/1988 | Steigerwald et al. |
| 4,730,635 A | 3/1988 | Linden |
| 4,787,406 A | 11/1988 | Edwards et al. |
| 4,913,401 A | 4/1990 | Handke |
| 4,932,629 A | 6/1990 | Rodomista et al. |
| 4,932,938 A | 6/1990 | Goldberg et al. |
| 4,935,010 A | 6/1990 | Cox et al. |
| 4,960,259 A | 10/1990 | Sunnanvader et al. |
| 5,017,192 A | 5/1991 | Dodge et al. |
| 5,020,562 A | 6/1991 | Richmond et al. |
| 5,022,422 A | 6/1991 | di Palma |
| 5,083,561 A | 1/1992 | Russo |
| 5,098,406 A | 3/1992 | Sawyer |
| 5,151,019 A | 9/1992 | Danby et al. |
| 5,219,327 A | 6/1993 | Okada |
| 5,232,193 A | 8/1993 | Skakoon |
| 5,238,218 A | 8/1993 | Mackal |
| 5,254,083 A | 10/1993 | Gentelia et al. |
| 5,257,978 A | 11/1993 | Haber et al. |
| 5,265,847 A | 11/1993 | Vorhis |
| 5,300,044 A * | 4/1994 | Classey et al. ............... 604/250 |
| 5,336,174 A | 8/1994 | Daoud et al. |
| 5,351,932 A | 10/1994 | Von Herrmann |
| 5,391,144 A | 2/1995 | Sakurai et al. |
| 5,395,351 A | 3/1995 | Munsch |
| 5,396,925 A | 3/1995 | Poli |
| 5,437,642 A | 8/1995 | Thill et al. |
| 5,474,544 A | 12/1995 | Lynn |
| 5,482,446 A | 1/1996 | Williamson et al. |
| 5,514,102 A | 5/1996 | Winterer et al. |
| 5,531,713 A | 7/1996 | Mastronardi et al. |
| 5,556,386 A | 9/1996 | Todd |
| 5,578,070 A | 11/1996 | Utterberg |
| D389,228 S | 1/1998 | Winterer et al. |
| 5,704,584 A | 1/1998 | Winterer et al. |
| 5,720,721 A | 2/1998 | Dumas et al. |
| 5,807,312 A | 9/1998 | Dzwonkiewicz |
| 5,810,323 A | 9/1998 | Winterer et al. |
| 5,826,621 A | 10/1998 | Jemmott |
| 5,971,357 A | 10/1999 | Denton et al. |
| 6,017,332 A | 1/2000 | Urrutia |
| 6,048,331 A | 4/2000 | Tsugita et al. |
| 6,092,695 A | 7/2000 | Loeffler |
| 6,129,699 A | 10/2000 | Haight et al. |
| 6,142,979 A | 11/2000 | McNally et al. |
| 6,183,447 B1 | 2/2001 | Urrutia |
| 6,196,922 B1 | 3/2001 | Hantschk et al. |
| 6,196,992 B1 | 3/2001 | Keilman et al. |
| 6,209,538 B1 | 4/2001 | Casper et al. |
| 6,261,262 B1 | 7/2001 | Briggs et al. |
| D455,489 S | 4/2002 | Beck et al. |
| 6,398,758 B1 | 6/2002 | Jacobsen et al. |
| 6,398,780 B1 | 6/2002 | Farley et al. |
| 6,461,335 B1 | 10/2002 | Noecker |
| 6,494,864 B1 | 12/2002 | Kerwin et al. |
| 6,595,950 B1 | 7/2003 | Miles et al. |
| 6,623,447 B2 | 9/2003 | Miles et al. |
| H2090 H | 11/2003 | Walker |
| 6,685,670 B2 | 2/2004 | Miles et al. |
| 6,749,591 B1 | 6/2004 | McNally et al. |
| D503,978 S | 4/2005 | Beck |
| 6,923,785 B2 | 8/2005 | Miles et al. |
| 6,979,311 B2 | 12/2005 | Miles et al. |
| 7,150,727 B2 | 12/2006 | Cise et al. |
| 7,168,444 B2 * | 1/2007 | Sesser et al. ............... 137/505.25 |
| 7,367,963 B2 | 5/2008 | Cise et al. |
| 2002/0127708 A1 | 9/2002 | Kluttz et al. |
| 2002/0169424 A1 | 11/2002 | Miles et al. |
| 2004/0097885 A1 | 5/2004 | Beck et al. |
| 2004/0220542 A1 | 11/2004 | Cise et al. |
| 2004/0260332 A1 | 12/2004 | Dubrul et al. |
| 2005/119625 A1 | 6/2005 | Miles et al. |
| 2006/0058740 A1 | 3/2006 | Cise et al. |
| 2006/0173412 A1 * | 8/2006 | Susi ............................. 604/123 |
| 2008/0065008 A1 | 3/2008 | Barbut et al. |
| 2008/0276911 A1 | 11/2008 | Woody |

FOREIGN PATENT DOCUMENTS

| | | |
|---|---|---|
| EP | 0 423 978 | 10/1990 |
| EP | 0 483 794 | 10/1991 |
| GB | 2 338 759 | 12/1999 |
| WO | WO 96/08666 | 3/1996 |
| WO | WO 96-17636 | 6/1996 |

* cited by examiner

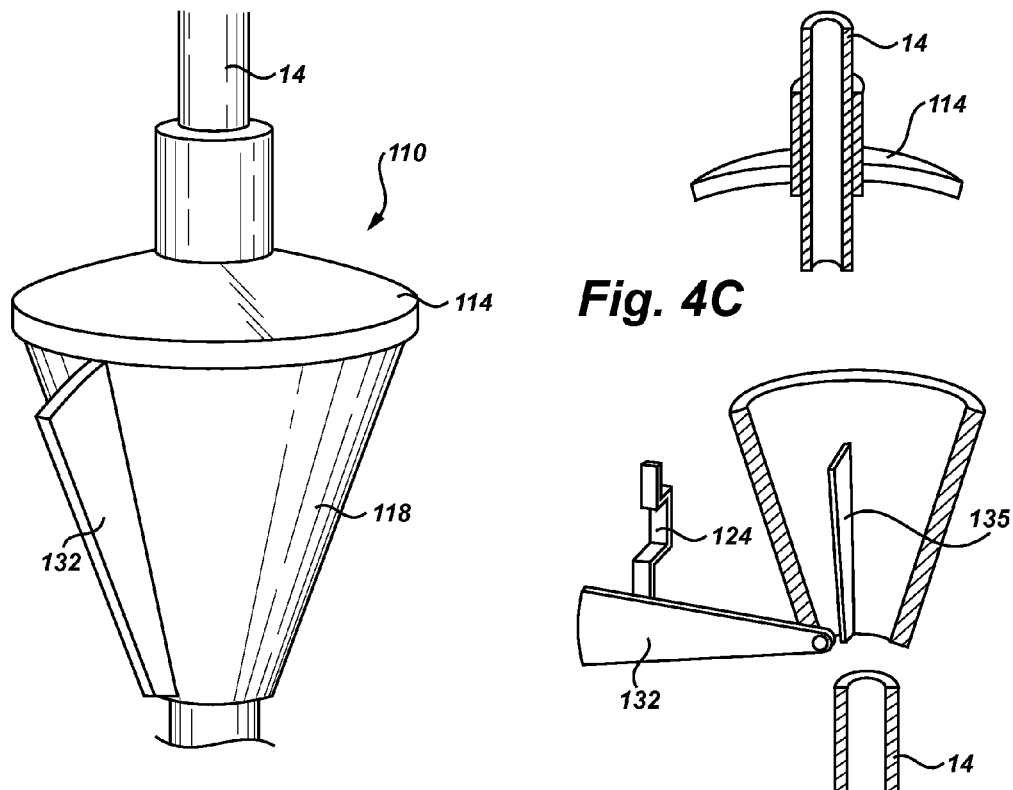
Fig. 4C
Fig. 4A
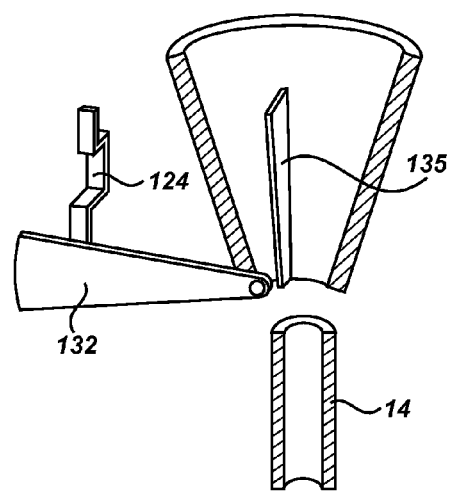
Fig. 4D
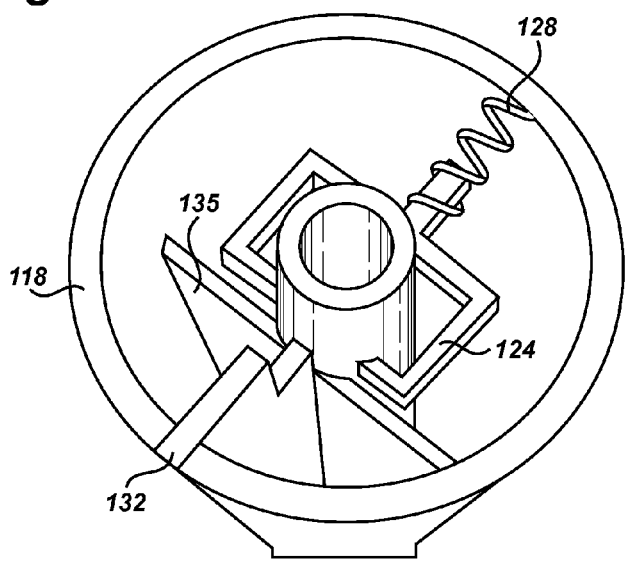
Fig. 4B

SECTION A-A

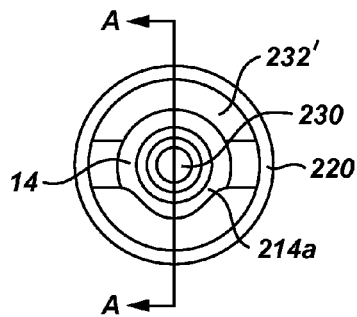
Fig. 9B
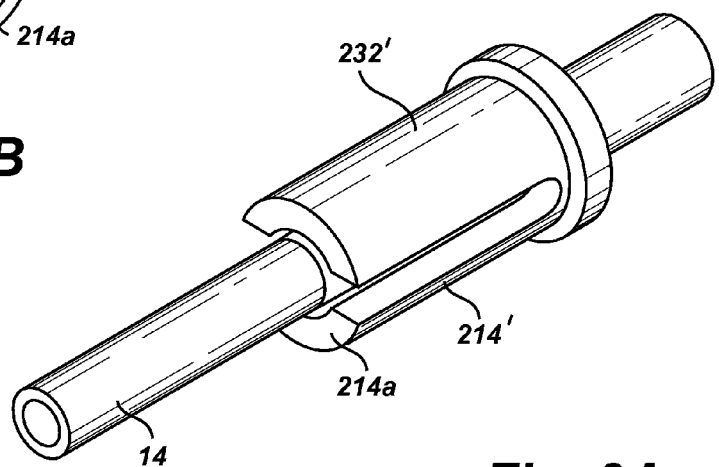
Fig. 9A
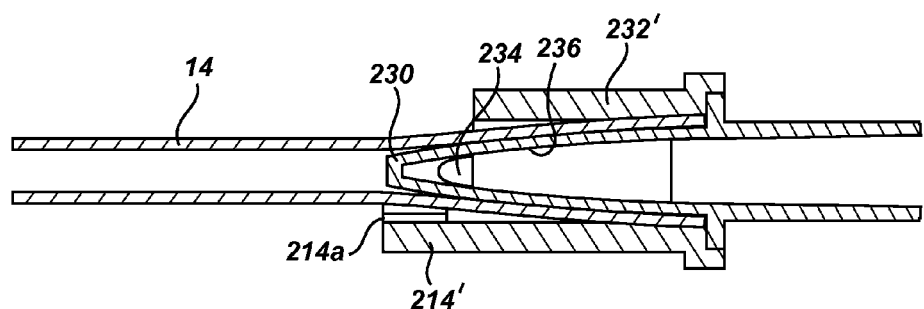
Fig. 9C  SECTION A-A

SECTION A-A

SECTION A-A

ANTI-FREE-FLOW MECHANISM FOR ENTERAL FEEDING PUMPS

PRIORITY

This application claims priority to U.S. Provisional Patent Application No. 61/041,561, filed Apr. 1, 2008, which is incorporated herein by reference in its entirety

FIELD

The present invention relates to mechanisms for preventing free-flow in an infusion pump. More particularly, the present invention relates to methods and associated devices for preventing free-flow in an infusion pump while minimizing nuisance alarms.

BACKGROUND

The use of anti-free-flow devices with medical pumps is well known in the art. When a fluid is being infused into a patient, it is usually desirable for the rate of flow to be regulated. It is disadvantageous in many circumstances to have a condition, commonly referred to as free-flow, in which flow into the patient is controlled solely by the force of gravity. Such conditions can result in a large volume of solution being infused into a patient over a very short period of time. Due to medical conditions or medication contained in the infused solution, a free-flow condition can pose health concerns to a patient. In some situations it can even result in the death of the patient.

Because of these concerns, numerous devices have been developed to regulate free-flow in medical pumps. For example, several different anti-free-flow devices are shown in U.S. Pat. No. 7,150,727, which is incorporated herein by reference. FIG. 13E of the '727 patent shows an in-line occluder disposed in tubing which is mounted on an existing enteral feeding pump. The infusion set includes a drip chamber which anchors one side of the tubing upstream from the pump rotor and an in-line occluder/connector which is used to mount the other side downstream from the pump rotor. The drip chamber and the in-line occluder/connector keep the tubing in tension against the pump rotor so that rotation of the rotor pumps fluid through the infusion set.

One challenge with the use of anti-free-flow devices is retrofitting presently existing pumps. While newer pump models are typically designed to accommodate anti-free-flow devices, pumps that are already in existence may lack such structures. One concern with occluders used with some existing pumps is that a free-flow condition can occur if the infusion set is not properly mounted in the pump. For example, if the occluder is mounted in a mounting structure and moved into an open position to allow flow but the infusion set is not properly wrapped around the rotor of the pump, there is nothing to control the rate of flow through the infusion set.

One solution to this problem has been the use of in-line occluders such as that shown in the '727 patent. An in-line occluder is placed and designed to prevent free-flow unless sufficient force is developed to expand the tubing sufficiently to allow flow past the occlude, or for an external structure to apply force to the infusion set and thereby open a channel between the infusion set and the occluder.

One problem with in-line occluders is that many older enteral feeding pumps develop relatively low pumping pressures. Because of this, the pumping pressure is occasionally inadequate to overcome the occluder or requires sufficient force that the pump inaccurately determines that there is an undesired occlusion downstream from the pumping mechanism. This causes the generation of an alarm which requires the response of medical personnel to determine that the tubing is in fact not occluded. These nuisance alarms waste the time and effort of medical personnel and unnecessarily disrupt the infusion process.

For example, as shown in FIG. 1, a known occluder 1 is disposed in the tubing 2 of an infusion line and mounted in an existing pump 3 as generally done with pumps such as the pump 3. The tubing is held in tension at one end by a drip chamber 4 at one end and by a connector 5 associated with the occluder 1 at the other. Between the drip chamber 4 and the connector 5, the tubing is wrapped about a pump rotor 6 which engages the tubing to drive a solution through the tubing.

The occluder 1 is advantageous over many other occluders because it will prevent flow through the infusion tubing if the tubing is inadvertently removed from the pump rotor. Other occluders, such as some pinch clip occluders, are opened when the tubing 2 is mounted on the pump and will not close if the tubing becomes loose.

One issue with the occluder 1 configuration is nuisance occlusion alarms. Many older pumps, such as the pump 3, have relatively low pumping power and will detect on undesired occlusion downstream based simply on the pressure needed to bypass the in-line occluder. Thus, it is desirable to have an occluder mechanism which will allow flow without nuisance alarms when the infusion set is properly mounted on the pump, and which will prevent a free-flow condition through the line if the tubing comes off the pump rotor or is otherwise not properly engaging the rotor.

While consideration has been given to simply opening the occluder when the infusion set is mounted on the pump, this still leaves open the risk of a free-flow situation. If the infusion line were inadvertently removed from around the rotor, the rotor would no longer act on the infusion line to control fluid flow. Thus, a free-flow situation could develop, potentially injuring the patient. Thus, there is a need for an apparatus and method for providing protection against a free-flow condition while avoiding nuisance alarms.

SUMMARY

An anti-free-flow mechanism for use with a medical pump and associated methods of use is disclosed. Embodiments of an anti-free-flow mechanism may include an occluder mechanism mounted on or in the infusion line which is biased into a closed position and which, when mounted on the pump, is opened as the infusion set is wrapped in tension around the rotor of the pump. The occluder mechanism may be configured to allow flow through the infusion tube as long as the tubing around the pump is in tension. In the event that tension is no longer present in the infusion pump around the tube, the occluder mechanism closes once again and prevents fluid from flowing through the tubing. Thus, flow through the tubing is not prevented as long as the tubing is properly mounted on the pump, but is terminated in the event that the tubing becomes loose.

According to some embodiments, the safety occluder is formed as a pinch clip which is biased so that the exterior of the tubing is pinched closed to prevent flow. Mounting the infusion set on the pump causes the pinching mechanism to be moved open. However, if the tubing is somehow removed from the rotor so that the infusion set is no longer in tension, the biasing element will return the pinching mechanism to an occluding orientation and thereby prevent fluid flow.

In other embodiments, a pinching mechanism is used to apply force to the tubing and thereby open a flow path past an in-line occluder when the infusion set is properly mounted in an infusion pump. However, when tension is released from the infusion set, the force on the tubing is released and flow through the infusion set is again stopped.

BRIEF DESCRIPTION OF THE DRAWINGS

Various embodiments are shown and described in reference to the numbered drawings wherein:

FIG. 4A shows a perspective view of an exemplary embodiment of an occluder mechanism;

FIG. 4B shows a top view of the base of the occluder mechanism of FIG. 4A with the top removed to show the occluder acting on a portion of tubing of the infusion set;

FIG. 4C shows a cross-sectional view of the top of the occluder mechanism of FIG. 4A and a portion of tubing;

FIG. 4D shows a cross-sectional view of the base portion of the occluder mechanism of FIG. 4A, with the occluder extended for visibility;

FIG. 9A shows a perspective view of and exemplary embodiment of yet another occluder mechanism;

FIG. 9B shows an end view of the occluder of FIG. 9A;

FIG. 9C shows a side cross-sectional view of the occluder of FIGS. 9A and 9B taken along line A-A;

It will be appreciated that the drawings are illustrative and not limiting of the scope of the invention which is defined by the appended claims. The various elements in the illustrated embodiments are exemplary and not comprehensive of all possible variations and embodiments. It is appreciated that not every element can be clearly displayed in a single drawing, and as such every drawing may not show each and every element of each embodiment.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
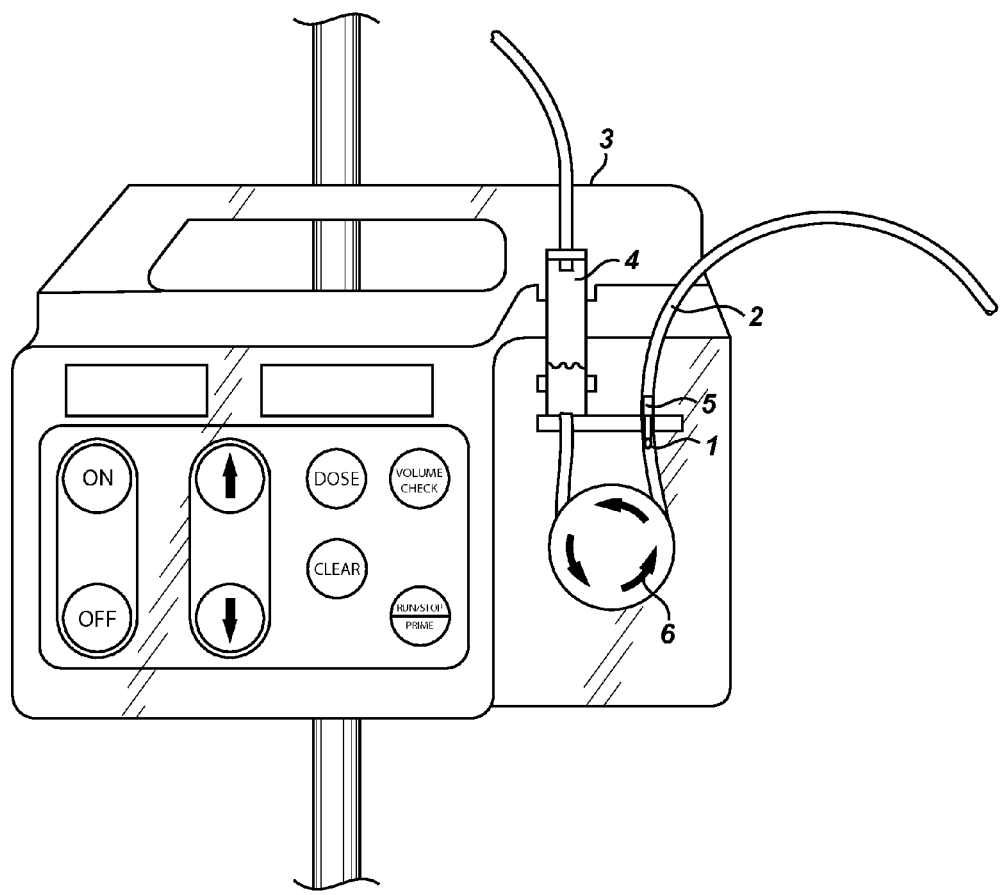
FIG. 1 shows a common enteral feeding pump having an in-line occluder disposed therein in accordance with the prior art.
Figure 2B:
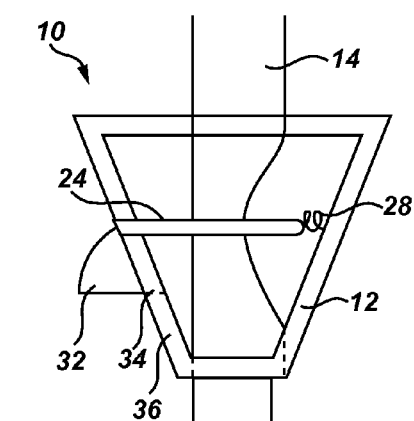
FIG. 2B shows a close-up view of the actuator and slide shown in FIG. 2A.
Figure 2B:
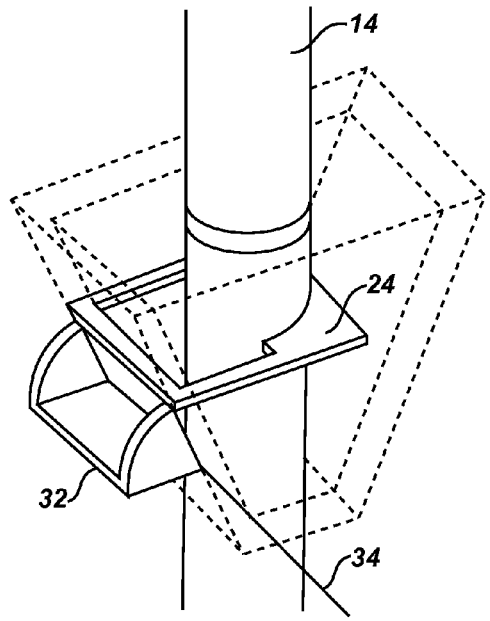
Figure 2A:
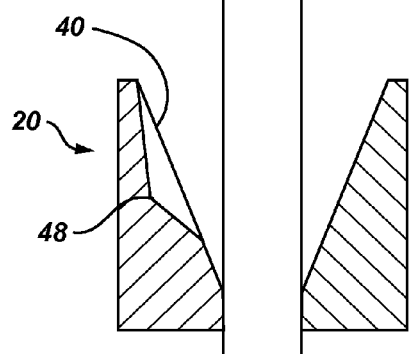
FIG. 2A shows a plan view of an exemplary occluder mechanism according to embodiments of the invention and a mounting structure configured for receiving the occluder mechanism.

Turning now to FIG. 2A, a cut-away view of an occluder mechanism 10 is illustrated, which is configured for placement along a segment of tubing 14 of an infusion set. FIG. 2A also shows a cross-sectional view of a mounting structure, generally indicated at 20 for use on a medical pump, such as the enteral feeding pump shown in FIG. 1. (As will be explained in additional detail below, the mounting structure 20 may be an adaptor which is a separate piece from the pump itself, or it can be the mounting structure on the pump which is traditionally used to load an infusion set.)

The occluder mechanism 10 may include a plunger or slider 24 which engages the tubing 14. A biasing element 28, such as a spring, may bias the slider 24 into engagement with the tubing 14 so as to pinch the tubing closed and thereby occlude the tube and prevent flow therethrough. Thus, the occluder mechanism 10 may be biased in a closed position which prevents flow.

An actuator 32, typically in the form of a pivot clip, may be disposed in engagement with the slider 24. Movement of the actuator 32, e.g. rotation of the pivot clip about an axis 34 (FIG. 2B), moves the slider 24 against the bias of the biasing element 28, and causes the slider to no longer pinch the tubing in a closed position. Thus, movement of the actuator 32 allows flow through the tubing 14.

The occluder mechanism 10 has at least one sloped sidewall 36 which is configured to allow the occluder mechanism to nest in the mounting structure 20 so that the sloped sidewall 36 engages a sloped sidewall 40 of the mounting structure 20 or some other structure in the sidewall. As the tapered occluder mechanism 10 slides into the tapered opening in the mounting structure 20, the wall 40 helps to center the occluder mechanism.

Figure 2C:
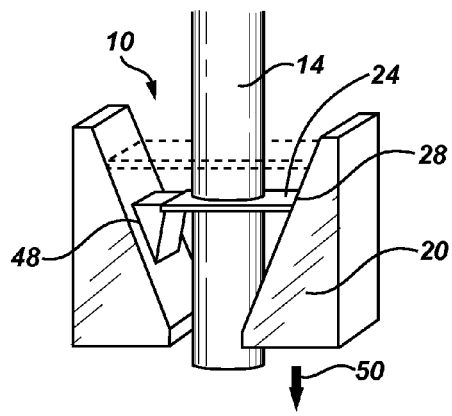
FIG. 2C shows a view of the occluder mechanism of FIG. 2A disposed in the mounting structure.

The wall 40 or a portion thereof may also engage the actuator 32 and push it inwardly into the occluder mechanism 10. This causes the slider 24 to move out of the closed, pinching position and into an open, non-occluding position where flow through the tubing 14 is enabled. Thus, mounting the occluder mechanism 10 in the mounting structure 20 opens flow through the tubing, as shown in FIG. 2C. (While the actuator 32 is shown as being generally L-shaped, it may be triangular or a number of other shapes in cross-section to facilitate pivoting and movement of the slider 24).

The engagement of actuator 32 and the sidewall 40 of the mounting structure 20, however, prevents the occluder mechanism 10 from remaining in the mounting structure in the event that the tubing 14 is not properly loaded. The biasing element 28 provides a force against the slider 24, and thus against inward movement of the actuator 32. If an external force is not applied to the occluder mechanism 10, the biasing element 28 will cause the occluder mechanism (via the slider 24 and actuator 32) to push against the mounting structure 20 to move upwardly, thereby returning the slider 24 into the occluding position. To overcome this biasing, the tubing 14 is placed in tension when it is wrapped around the rotor of the pump as represented by the arrow 50 in FIG. 2C. (In other pump configurations, the tension on the tubing may be created by a mounting structure mounting in the pump or by use of a drip chamber, which is spaced sufficiently away from the occluder mechanism 10 and mounting structure 20, that the tubing 14 is placed in tension when properly mounted in the pump).

If the tension on the tubing 14 is relieved, i.e. if the tubing inadvertently comes off the pump rotor, the lack of downward pull on the tubing represented by arrow 50 disappears and the bias of the biasing element 28 on the slider 24 and actuator 32 overcomes the effect of gravity on the occluder mechanism 10 and the pushes the occluder mechanism 10 upwardly in the mounting structure 20. This returns the actuator 32 to its original position and allows the slider 24 to occlude flow. It will be appreciated that the actuator 32 need not return the occluder mechanism 10 to the top of the mounting structure. Rather, the actuator 32 need only push the occluder mechanism upwardly sufficiently for the slider 24 to occlude flow through the tubing. This can be assisted by a void 48 in the sidewall 40 of the mounting structure 20.

It will be appreciated that the mounting structure 20 may be mounted on any number of different pumps in a variety of ways. Some pumps, such as that shown in FIG. 1, already include a structure downstream from the pump rotor on which the mounting structure 20 can be mounted. Other pumps may require the mounting structure to be adhesively or otherwise attached. Such attachments will be apparent to those of skill in the art and are not discussed herein in detail.

Figures 3A, 3B:
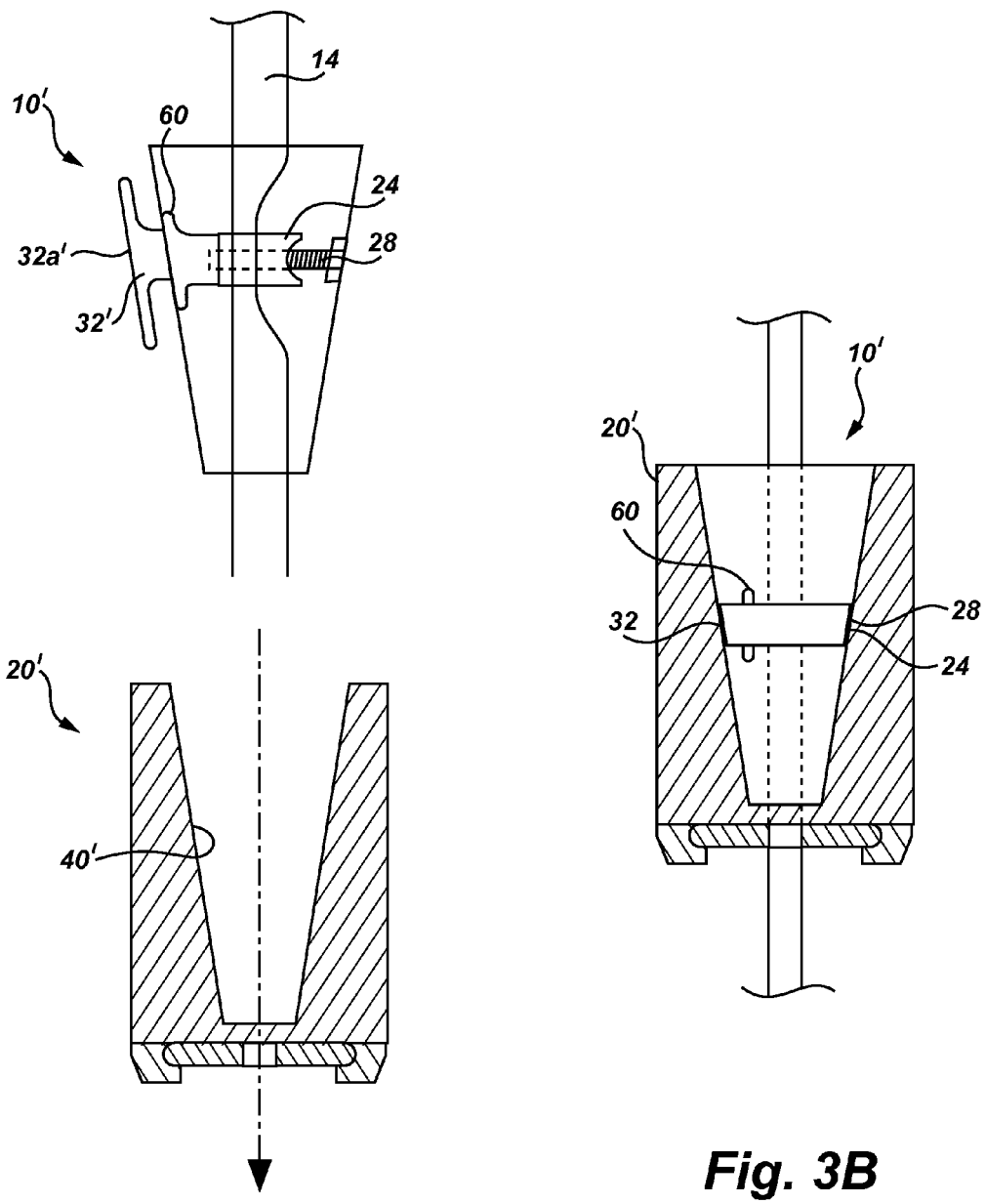
FIG. 3A shows a cross-sectional view of an exemplary occluder mechanism and mounting structure.
FIG. 3B shows the occluder mechanism of FIG. 3A mounted in the housing so as to allow flow through the infusion tubing.

Turning now to FIGS. 3A and 3B, there is shown an alternate configuration of an occluder mechanism 10' and a mounting structure 20'. The occluder mechanism 10' is mounted on a segment of tubing 14 of an infusion set. Like the occluder mechanism 10 of FIGS. 2A-2C, the occluder mechanism 10' includes a slider 24 which is biased by a biasing element 28 into a closed or occluding position where the slider 24 pinches closed the tubing 14. Rather than a pivoting actuator 32 in FIGS. 2A-2C, the occluder mechanism 10' in FIGS. 3A-3B has an actuator 32' which moves linearly to move the slider 24 out of the first, closed or occluding position and into a second, open or non-occluding position.

The mounting structure 20' includes a sloped wall 40' which interacts with a sloped wall 32a' on the actuator 32' As the occluder mechanism 10' is drawn down into the mounting structure 20', the wall 32a' interacts with wall 40' and pushes against the biasing element 28 to move the slider 24 into the open position. Due to the force of the biasing element 28, however, a downward force must be placed on the occluder mechanism 10' to overcome the bias. This is done by the tension on the tubing 14. If the tension is released, the biasing element 28 will push against the slider 24, which will force the actuator 32 outwardly. The sloped interaction between the mounting structure 20' and the wall 32a' of the actuator 32 will cause the occluder mechanism 10' to rise sufficiently that tubing 14 is pinched closed by the slider 24'.

It will be appreciated that the housing 12 of the occluder mechanism 10 or 10' need not be sloped. Likewise, the entire wall 40, 40' need not be sloped. Rather, only portions may be needed on the mounting structure 20 or 20' and the actuator 32 or 32', which interact to allow for conversion of the force of the biasing element 28 into movement of the occluder mechanism 10, 10' when the tubing 14' is not in tension.

FIGS. 3A and 3B also show a stop 60 disposed on the slider 24. The stop 60 is disposed to prevent the slider 24 from coming out of the occluder mechanism 10' if the tubing is not present. It also prevents the slider 24 from overly pinching the tube when the occluder mechanism 10' is not disposed in the mounting structure 20'.

It will be appreciated that the interior of the occluder mechanism 10 or 10' may include a wall disposed on one side of the tubing 14 to aid the slider 24 to pinch closed the tubing. In other words, one side of the tubing 14 is held by the wall and the opposing side is engaged by the slider 24 to pinch the tubing closed.

Turning now to FIG. 4A, embodiments of and occluder mechanism 110 are illustrated. The occluder mechanism 110 includes a top 114 and a base 118. As shown in FIG. 4C, the top 114 can be used to secure the occluder mechanism 110 into a segment of tubing 14 of an infusion set. This can be accomplished by a variety of mechanisms, including using an adhesive.

The occluder mechanism 110 also includes a base 118. The base 118 may be configured to nest in a mounting structure, such as mounting structure 20' in FIGS. 3A and 3B. However, it will be appreciated that other configurations can be used for the mounting structure while still accomplishing the selective termination of fluid flow through the tubing 14 as described herein.

The base 118 may include an actuator 132 which pivotably extends from the base. As shown in FIG. 4B, the actuator 132 is attached to a plunger or slide 124 which engages the tubing 14 to selectively terminate flow. The slide 124 is biased into a first, closed position by a biasing element 128, such as a spring. When no other force is acting on the slide 124, the slide is forced into the side of the tubing 14, thereby pinching the tubing closed. When in this state, the actuator 132 will extend from the side of the base 118 as shown in FIG. 4A. However, application of a force to the actuator 132 to move it into the position shown in FIG. 4B, moves the slide 124 against the bias of the biasing element 128 and away from the tubing 14, thereby allowing flow through the tubing.

Because of the slope presented by the far end of the actuator 132 when it is extended, extending the actuator will tend to lift the base out of the mounting structure (e.g. mounting structure 20' in FIG. 3). As the base 118 is lifted, the actuator 132 is able to continue to move outwardly and the slide 124 forcefully engages the tubing. Thus, unless the base 118 is secured in the mounting structure 20', etc., the biasing element 128 will cause the slide 124 to pinch closed the occluder. The base 118 is secured in the mounting structure by having the tubing 14 be in tension in a direction which will hold the occluder mechanism 110 in place.

Such a configuration may be highly advantageous in the context of a medical pump. If the infusion set is not properly loaded, the occluder mechanism 110 will remain with the plunger or slider 124 in the first, occluding position, thereby preventing a free-flow situation which could cause injury to the patient. Once the infusion set is properly loaded, the occluder mechanism 110 is moved into the second, open position where it will not interfere with the pump's operation and will be less susceptible to causing false occlusion alarms. In the event the tubing 14 is accidentally removed from proper placement on the pump (i.e. the tubing is inadvertently pulled off the rotor), the occluder mechanism is lifted or otherwise moved sufficiently to enable it to return to the occluding position. Thus, free-flow is avoided even when the tubing 14 is inadvertently removed from its proper position.

FIG. 4D shows a cross-sectional view of the base 118 with the actuator 132 and slider 124 pivoted out of the way to show a wall 135. The wall 135 helps secure the tubing 14 so that it can be pinched closed by the slide 124.

Figure 4E:
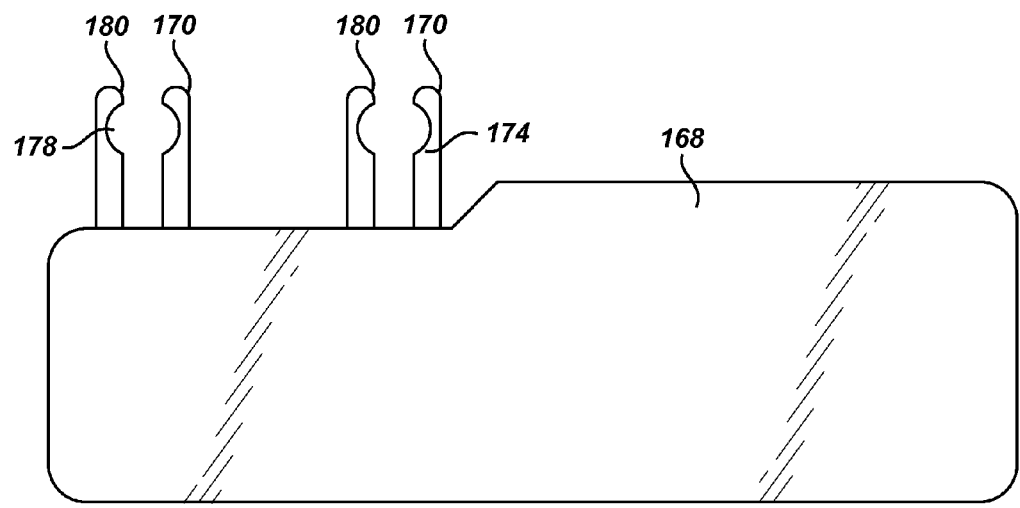
FIG. 4E shows a top view of a pump and the mounting structure which is used to secure the infusion set to the pump.

FIG. 4E shows a top view of a pump 168 similar to that shown in FIG. 1. While the mounting structure of the present invention may be an adapter for attachment on a pump, such as those shown regarding FIGS. 2A-3B, the mounting structure may also be the conventional mounting structure on a pump. For example, the COMPAT pump made by NESTLE uses two sets of mounts 170. One mount 174 is used to receive a drip chamber, while the other mount 178 is used to hold other structures, such as an adaptor for connecting a tubing segment which is worked by the pump rotor (not shown) to a longer, less expensive piece of tubing which connects to the patient via a stoma catheter, etc.

The mounts 174 and 178 include a receiving portion 180 which is tapered or generally frusto-conical (excepting the openings). The receiving portions can receive the occluder mechanism 10, 10' etc. and facilitate lifting of the occluder mechanism if tension is not maintained on the tubing. It will be appreciated that other pumps may have receiving portions which are not tapered. However, the actuator 32 or 32' can be configured to still engage the receiving portion and lift the occluder mechanism to thereby occlude flow.

Figure 5:
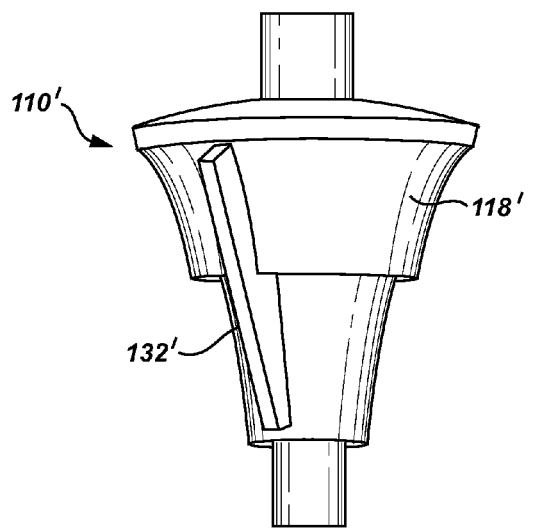
FIG. 5 shows a perspective view of an exemplary embodiment of an occluder mechanism.
Figure 6:
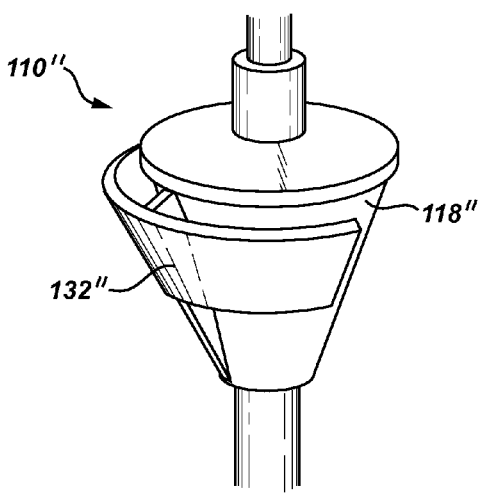
FIG. 6 shows a perspective view of an exemplary embodiment of an occluder mechanism.
Figure 7:
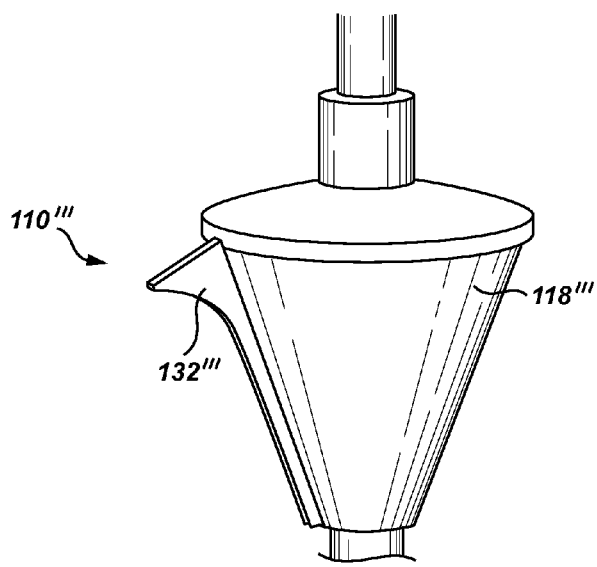
FIG. 7 shows a perspective view of yet another exemplary embodiment of an occluder mechanism.

FIG. 5, FIG. 6 and FIG. 7 each show a perspective view of embodiments of occluder mechanisms 110', 110" and 110' having different bases 118', 118" and 118' and/or various configurations of the actuator 132', 132" and 132'. The base and actuator can be configured so as to require a specific configuration of a mounting structure, or can be configured to allow a single occluder mechanism to be used with multiple pumps. For example, the base 118' is stepped so that it may be inserted into pumps having different sized receiving portion on the mounting structure. The actuator 132" may be used to prevent the occluder mechanism 110" from being inserted into the mounting structure designed for occluder mechanism 110'''.

Figure 8B:
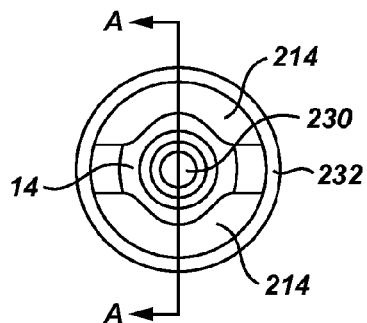
FIG. 8B shows an end view of the occluder mechanism of FIG. 8A.
Figure 8D:
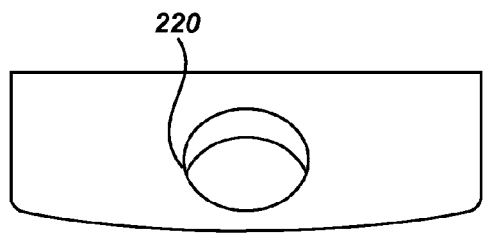
FIG. 8D shows a mounting structure for receiving the occluder mechanism shown in FIGS. 8A-8C.
Figure 8A:
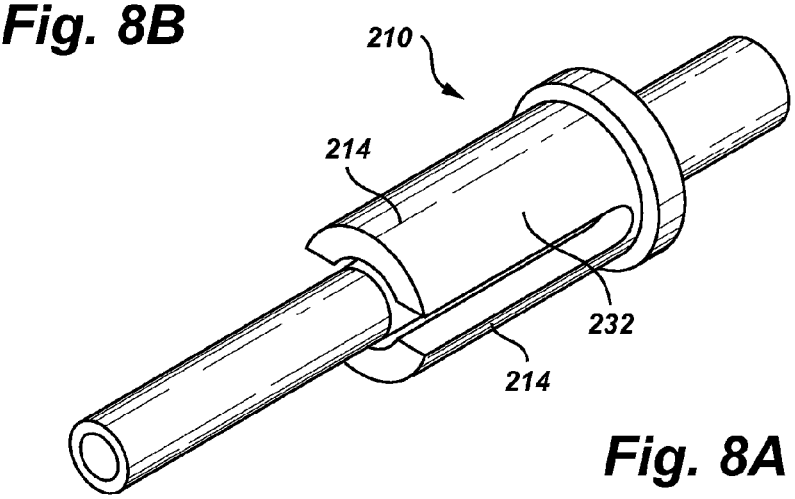
FIG. 8A shows a perspective view of still another configuration of an occluder mechanism.
Figure 8C:
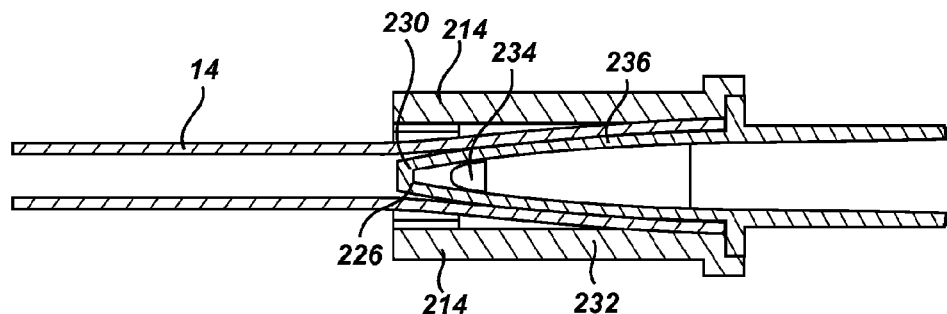
FIG. 8C shows a side cross-sectional view taken along line A-A in FIG. 8B.

Turning now to FIGS. 8A through 8D, there is shown an embodiment of an occluder mechanism that involves the use of an in-line occluder—i.e. an occluder which occludes flow by disposition inside of the tube, rather than by pinching the tubing closed. Referring specifically to FIG. 8C, there is shown a cross-sectional view of tubing 14 of an infusion set with an occluder 226 disposed inside the tubing. The occluder 226 includes a stop 230 which typically has an outer diameter which is slightly larger than the inner diameter of the tubing. The stop 230 prevents fluid flow through the tubing unless a flow channel is opened past the stop. (A more detailed description of such occluders is set forth in U.S. Pat. No. 7,150,727, which is incorporated herein by reference.) When a flow channel is open, the fluid flows past the stop 230 and into an opening 234 in a body 236 which can also serve as a connector for attaching segments of an infusion line. Once past the stop 230, the fluid is free to travel downstream through the channel in the body and through the remainder of the infusion set.

Opening a flow channel past the stop 230 can be accomplished in several ways. One common method is to simply provide sufficient pressure to radially expand the tubing 14 so that a flow path opens around the tubing. As mentioned in the background section, however, this method can create false alarms suggestion that the tubing is occluded downstream.

Another method to open a flow channel may be to apply force to the tubing adjacent the stop 230. When force is applied, the tubing tends to deform and open a flow channel around the stop 230. By controlling where the force is applied to the stop, the configuration of the openings can also be controlled as discussed in the '727 patent. Applying force on one side can create a single channel, while applying force on opposing sides will create a flow channel on each side perpendicular to the application of force.

In FIG. 8A, the occluder mechanism 210 may include a body forming an actuator 232 in the form of a pair of arms 214. The arms 214 are bendable or pivotable to engage the stop 230 when they are mounted in a mounting structure 220 (FIG. 8D or 170 in FIG. 4E) to open fluid flow past the stop.

While it operates with an in-line occluder rather than a pinch occluder, the occluder mechanism 210 can function similarly to those discussed above in that when the occluder mechanism 210 is disposed in the mounting structure 170 or 220 and tension is applied, the tubing is opened for fluid flow controlled by the pump. If, however, tension is not present on the tubing, the biasing of the arms 214 (like the biasing element 128) will allow the tubing to be returned to an occluded orientation. Alternatively, the occluder mechanism 210 can be configured so it nests in the mounting structure 170, 220 and remains open regardless of tension on the tubing—thereby forgoing automatic closure if the tubing 14 is not loaded properly. Whether the occluder mechanism 210 provides automatic closure will depend on the engagement between the occluder mechanism and the mounting structure.

If medical personnel need to temporarily open the occluder mechanism 10, 10', 110, 110', 110", 110''' or 210, he or she need only apply force to the actuator 32, 32', 132, 132', 132", 132''' or 232 to open flow through the tubing. As soon as the pressure is released, however, the flow past the occluder is terminated. Thus, the risk that medical personnel accidentally leave the tubing in a free-flow state is eliminated.

Turning now to FIG. 9A, there is shown an occluder mechanism 210' which is a variation of the occluder mechanism 210 of FIG. 8A. Rather than using a pair of arms 214 as the actuator 232 in the occluder mechanism of FIG. 8A, a single arm 214' acts as the actuator 232' and pivots into forceful contact with the tubing adjacent the stop 230 to open a flow channel past the stop. Additionally, as shown in FIG. 9C, the ends 214a of the arm 214' may have relatively sharp corners to engage the tubing 14 and help open the flow channel. One advantage of the configurations shown in FIGS. 8A through 9C is that they can be used with in-line occluders already in use with pumps such as that shown in FIG. 1, thus minimizing retooling.

Figure 10A:
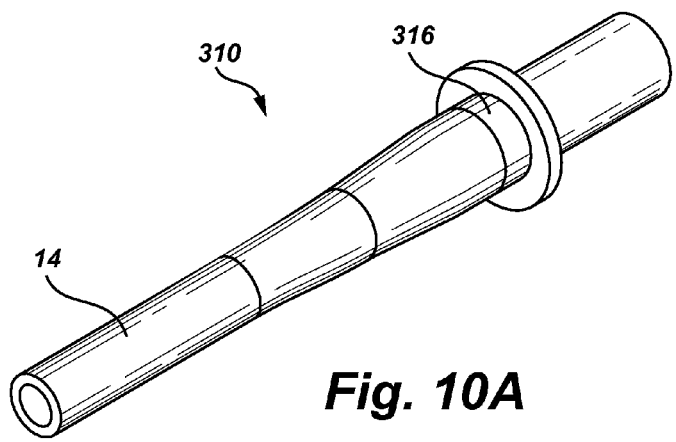
FIG. 10A shows a perspective view of yet another occluder mechanism along with infusion tubing.
Figure 10B:
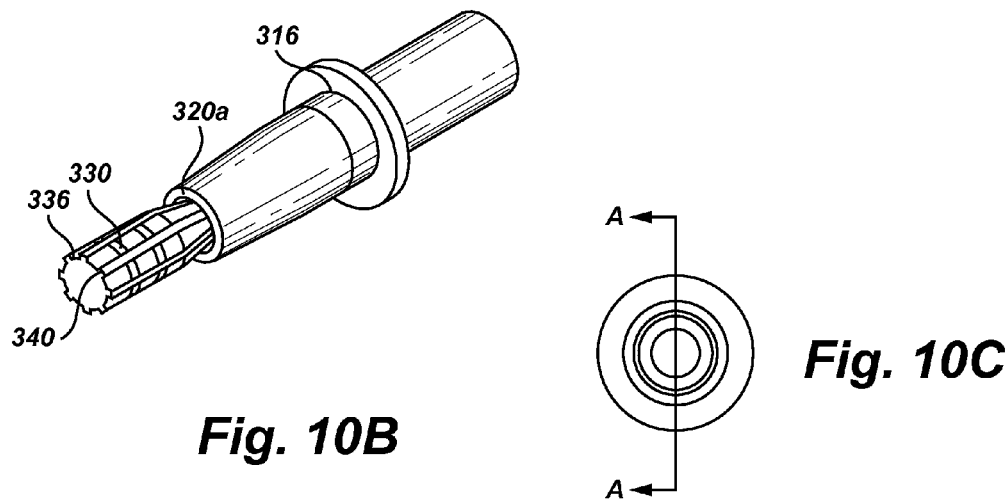
FIG. 10B shows the occluder mechanism of FIG. 10A with the infusion tubing removed to show the in-line occluder.

Turning now to FIGS. 10A-10E, there are shown various views of yet another occluder mechanism, generally indicated at 310, formed in accordance with principles of the present invention. The occluder mechanism 310 includes a connector 316 having a channel 320 extending therethrough. A stop 330 is disposed in a segment of an infusion set tubing 14 which attaches to the connector. FIG. 10B shows a perspective view of the stop 330 and the connector 316 with the tubing removed and which the stop 330 being disposed in a first, closed or occluding position.

The stop 330 has a plurality of projections 336 which are spaced apart to leave channels 340. The ends of the projections 336 are configured to remain in contact with the tubing 14, while the channels 340 allow fluid to flow along the stop for the distance for which the projections engage the tubing.

Figure 10C:
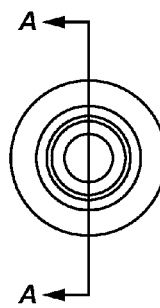
FIG. 10C shows an end view of the occluder mechanism of FIG. 10A.
Figure 10D:
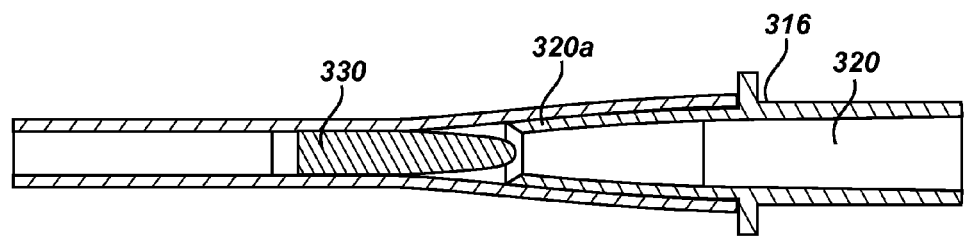
FIG. 10D shows a side cross-sectional view of the occluder mechanism of FIG. 10A with the in-line occluder in a closed configuration.

FIG. 10D shows is shown a side cross-sectional view of the stop 330 and connector 316 taken along lines A-A in FIG. 10C with the stop in a closed position. Downstream from the channels 340, the stop 330 is configured to seat in the opening to the channel 320 in the connector 316. Because the tubing 14 is usually elastomeric, the stop 330 can be placed in the tubing so that a small amount of force is applied to maintain the stop 330 seated in the opening 320a in the connector. In other words, the stop 330 is biased into a closed or occluding position. In this position, flow will not occur through the connector. Thus, the stop 330 remains in a first, closed or occluding position unless acted on by some external force.

Figure 10E:
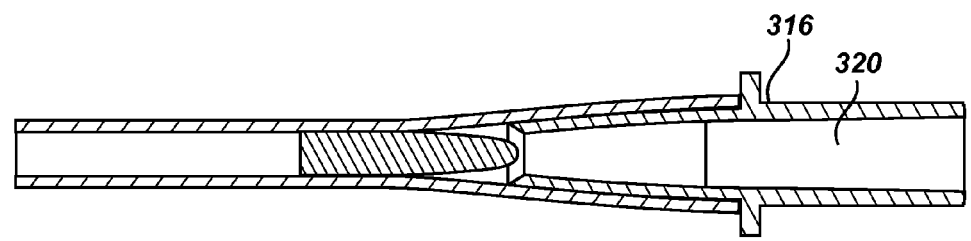
FIG. 10E shows a side cross-sectional view of the occluder mechanism of FIG. 10A with the in-line occluder in an open configuration.

When the tubing 14 is placed in tension by mounting on a pump, a portion of the tubing 14 distal from the connector 316 is pulled away from the connector. The elastomeric tubing will stretch and the stop 330 is pulled at least partially out of the connector 316 as shown in FIG. 10E. The projections 336 and channels 340 prevent the tubing from collapsing on the stop 330 sufficiently to prevent flow past the stop. Thus, the stop 330 is moved into a second, open or non-occluding position. As soon as the tension on the tubing is released, however, the stop 330 will be drawn back into the connector 316, thereby precluding flow.

Figure 11A:
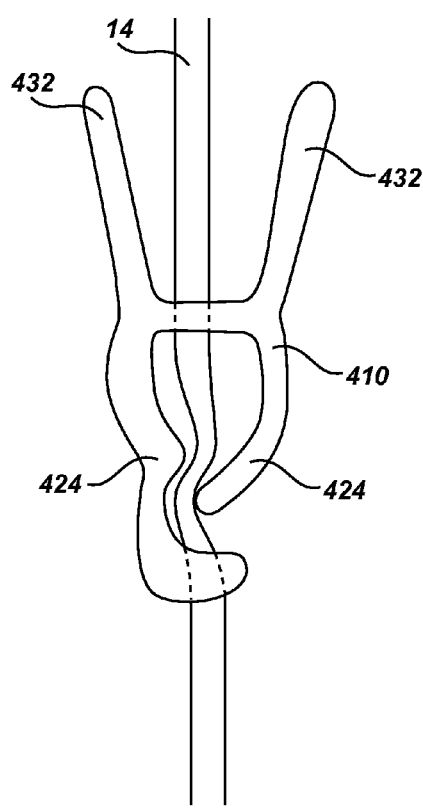
FIGS. 11A and 11B show yet another occluder mechanism and mounting structure for selectively preventing free-flow in an infusion set.

Turning now to FIG. 11A, there is shown a pinch clip occluder 410 mounted on a segment of infusion set tubing 14. The pinch clip occluder includes a pair of arms 424 which are biased to pinch closed the tubing 14. A pair of flanges 432 extends outwardly from the arms 424 such that pinching the flanges 432 draws the arms away from each other, thereby opening flow through the tubing 14.

Figure 11B:
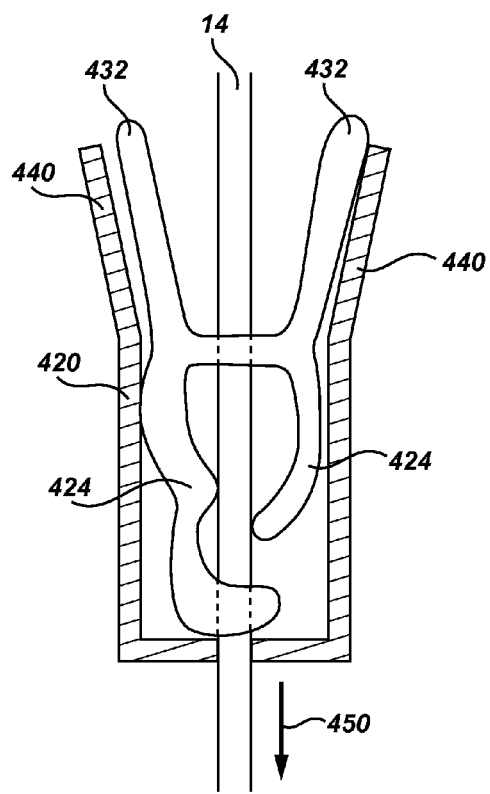

FIG. 11B shows the pinch clip occluder 410 mounted in a mounting structure 420. The mounting structure 420 has a pair of sloped walls 440 which engage the flanges 432 and push them toward one another to thereby pull apart the arms 424 and thereby open flow through the tubing 14. The slope of the wall 440, however, allows the natural bias of the flanges to urge the pinch clip occluder 410 out partially out of the housing 420. Thus, unless a force is applied by tension on the tubing, as represented by arrow 450, the flanges 432 will return to their original position and occlude flow through the tubing.

Figure 12A:
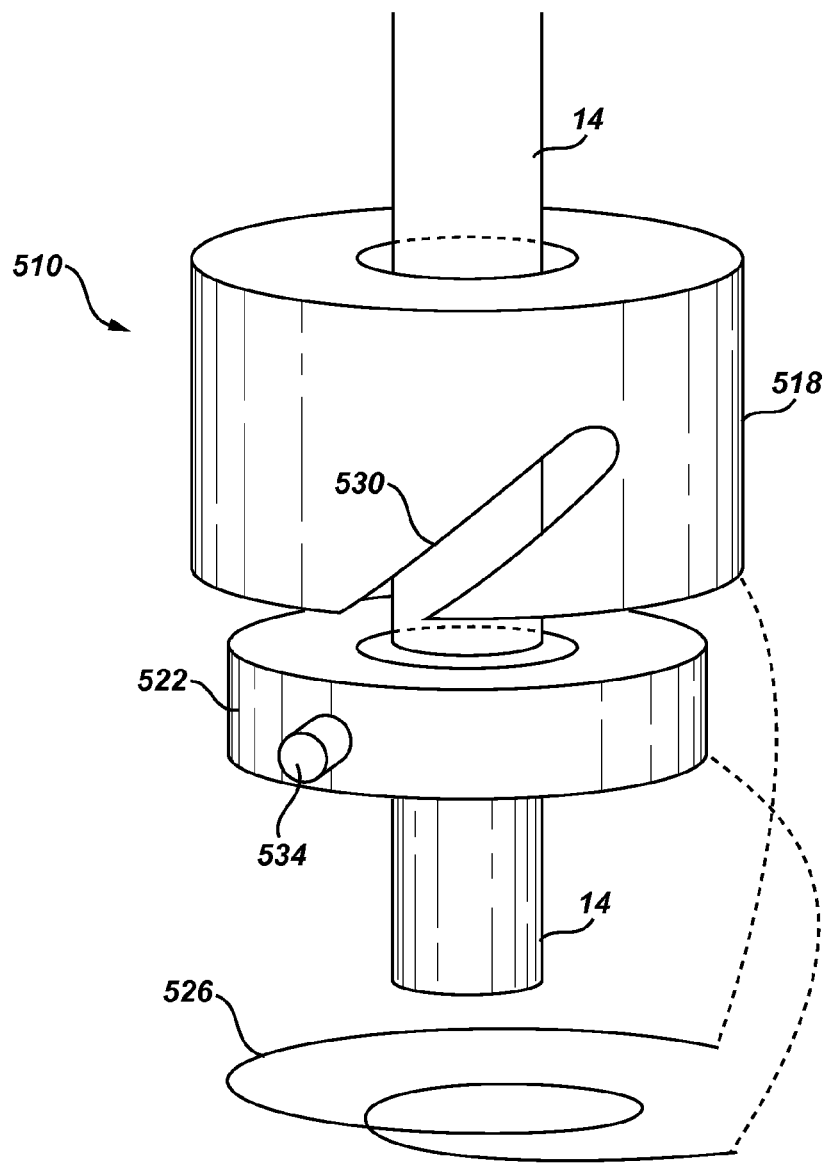
FIG. 12A shows an exploded view of yet another occluder mechanism.

FIG. 12A shows an exploded view of yet another occluder, generally indicated at 510, disposed along a segment of tubing 14 of an infusion set. Rather than using a plunger or slide, or an in-line occluder as the previous occluders, the occluder 510 includes a first body 518 and a second body 522, each of which is attached to the tubing 14. The first body 518 is also attached to the second body 522 by a torsional spring 526.

Figure 12B:
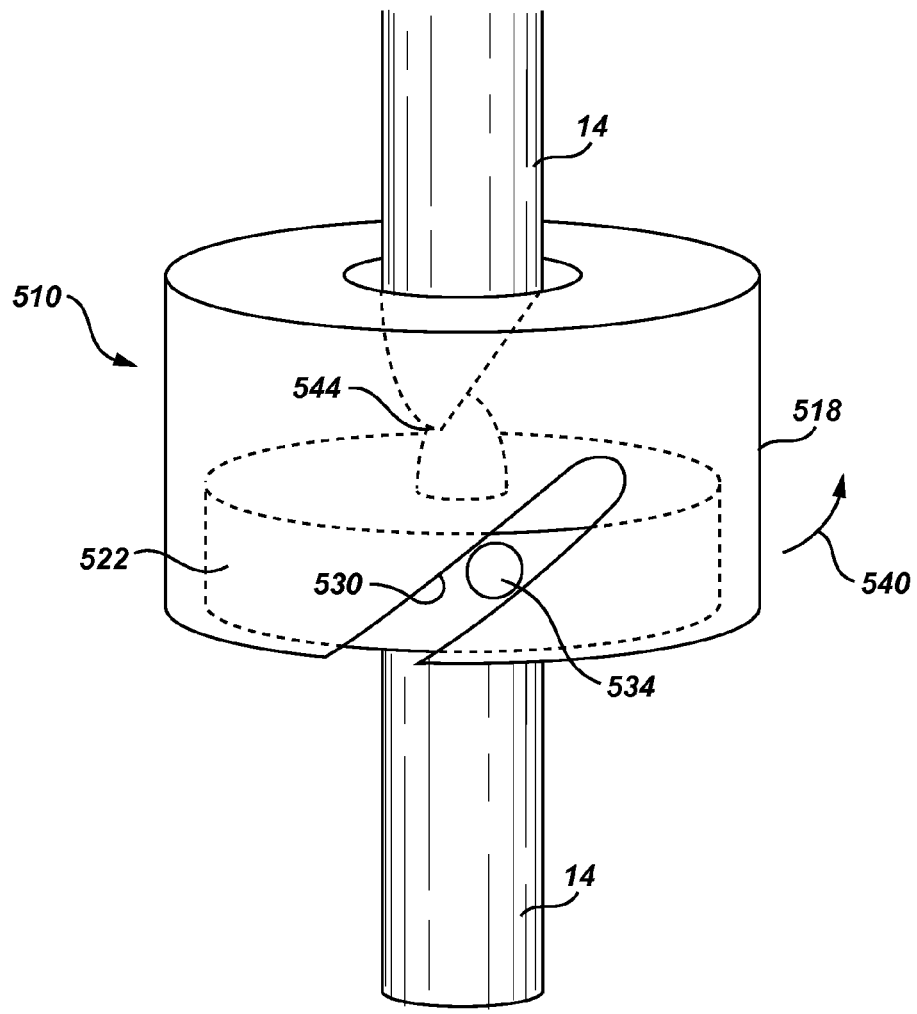
FIG. 12B shows the occluder mechanism of FIG. 12, with the occluder in a closed, occluding position.

The first body 518 also includes a channel 530 configured for receiving a projection 534 on the second body 522. The second body 522 is configured to nest in and travel helically in the first body 518 under a bias from the by the torsional spring 526. As the second body 522 moves upwardly, the projection 534 travels in the channel 530, causing the second body to rotate as shown by arrow 540 in FIG. 12B. Rotating the second body 522 also rotates that portion of the tubing 14 to which it is attached. The first body 518 and the portion of tubing to which it is attached, do not rotate however. Thus, as the second body 522 moves, the tubing 14 is twisted closed, (shown at 544 in FIG. 12B) thereby preventing free-flow through the tubing.

When the tubing 14 is mounted in a pump under tension, the downward force on the tubing 14 pulls against the bias of the torsional spring 526 (FIG. 12A). This pulls the second body 522 downwardly in the first body 518 and causes rotation of the second body due to the interaction of the channel 530 and projection 534. This rotation returns the tubing 14 to its normal, untwisted configuration and opens flow through the tubing 14. If tension on the tubing 14 is released, however, the torsional spring 526 will lift and turn the second body 522, thereby occluding flow through the tubing.

Thus there are disclosed embodiments of an anti-free-flow mechanisms and associated methods of use. Those skilled in the art will appreciate numerous modifications which can be made in light of the present disclosure that do not depart from the scope of the invention. The appended claims are intended to cover such modifications.

What is claimed is:

1. An occluder system, comprising:
    a segment of tubing of an infusion set;
    an occluder mechanism engaging the tubing and configured to reduce or prevent fluid flow through the tubing, the occluder mechanism having a body and an actuator, the actuator having a first, occluding position and a second, non-occluding position, the actuator being biased into the first position; and
    a mounting structure for receiving the occluder mechanism and for moving the actuator into the second, non-occluding position, the occluder mechanism being slidable longitudinally into the mounting structure in a direction parallel to tubing; and
    wherein the occluder mechanism is biased into the first, occluding position when not disposed in the mounting structure.

2. The occluder system of claim 1, wherein the biasing member pushes the actuator outwardly from the occluder body and thereby causes the occluder mechanism to slide at least partially out of the mounting structure unless an external force is applied to hold the occluder mechanism into the mounting structure.

3. The occluder system of claim 1, wherein the occluder body and mounting structure are generally conical in shape.

4. The occluder system of claim 1, wherein the actuator has an arm attached thereto, the arm engaging the tubing to selectively open and close a flowpath in the tubing.

5. The occluder system of claim 1, wherein the actuator is a separate structure from the body and is pivotably mounted to the body.

6. The occluder system of claim 1, wherein, when the occluder is mounted in the mounting structure, tension in the tubing holds the occluder into the mounting structure.

7. A method for selectively preventing a free-flow condition in an infusion set, the method comprising:
    providing an occluder mechanism disposed along a segment of tubing of an infusion set, the occluder mechanism having a body, an actuator, and a biasing mechanism, the actuator being biased outwardly from the body in a first, occluding position;
    mounting the occluder mechanism in a tapered mounting structure by moving the occluder mechanism into the mounting structure in a direction parallel to the tubing and thereby moving the actuator into a second, non-occluding position; and
    automatically moving the occluder mechanism out of the mounting structure to place the actuator in the first, occluding position unless an external force is applied to pull the occluder mechanism into the mounting structure.

8. The method according to claim 7, further comprising using tension on the tubing to hold the occluder mechanism in the mounting structure and in the second, non-occluding position.

9. The method according to claim 8, wherein the occluder mechanism and the mounting structure are configured such that release of tension on the tubing causes the occluder mechanism to move relative to the mounting structure and causes the actuator to return to the first, occluding position.

10. The method according to claim 7, wherein the occluder mechanism and mounting structure are tapered along a direction parallel to the tubing.

11. The method according to claim 10, further comprising moving the actuator inwardly to move the occluder mechanism into the second, non-occluding position, and forcing the actuator to move outwardly to thereby move the occluder mechanism relative to the mounting structure and return the occluder mechanism to the first, occluding position.

12. The method according to claim 7, wherein the occluder mechanism includes a pinch clip occluder.

13. The method according to claim 7, wherein the mounting structure has a tapered cavity defined by sloped walls, and wherein the method comprises disposing the occluder body and actuator in the cavity and holding the occluder in the mounting structure by applying tension to the tubing.

14. The method of claim 7, wherein the step of mounting the occluder mechanism in a tapered mounting structure more specifically comprises moving the body and actuator of the occluder mechanism into a tapered mounting structure cavity in a direction parallel to the tubing and thereby move the actuator into the second, non-occluding position.

* * * * *